(12) United States Patent
Qin et al.

(10) Patent No.: US 10,039,798 B2
(45) Date of Patent: Aug. 7, 2018

(54) EXTRACTS OF ROSEMARY OR HEMEROCALLIS FULVA AND METHODS OF USING SAME TO PROMOTE CIRCADIAN RHYTHM

(71) Applicant: IN Ingredients, Inc., Columbia, TN (US)

(72) Inventors: Bolin Qin, Gaithersburg, MD (US); Augustin T. Romero, Columbia, TN (US); Tim Romero, Columbia, TN (US)

(73) Assignee: IN Ingredients, Inc., Columbia, TN (US)

( * ) Notice: Subject to any disclaimer, the term of this patent is extended or adjusted under 35 U.S.C. 154(b) by 294 days.

(21) Appl. No.: 15/036,479

(22) PCT Filed: Nov. 13, 2014

(86) PCT No.: PCT/US2014/065336
§ 371 (c)(1),
(2) Date: May 13, 2016

(87) PCT Pub. No.: WO2015/073598
PCT Pub. Date: May 21, 2015

(65) Prior Publication Data
US 2016/0296581 A1 Oct. 13, 2016

Related U.S. Application Data

(60) Provisional application No. 61/903,434, filed on Nov. 13, 2013, provisional application No. 61/903,440, filed on Nov. 13, 2013.

(51) Int. Cl.
| | | |
|---|---|---|
| *A61K 36/00* | (2006.01) |
| *A61K 36/53* | (2006.01) |
| *A61K 36/896* | (2006.01) |
| *A23K 20/105* | (2016.01) |
| *A23K 20/158* | (2016.01) |
| *A23K 20/10* | (2016.01) |
| *A23L 33/105* | (2016.01) |
| *A61K 31/56* | (2006.01) |
| *A61K 36/88* | (2006.01) |
| *A61K 31/19* | (2006.01) |

(52) U.S. Cl.
CPC ............. *A61K 36/53* (2013.01); *A23K 20/10* (2016.05); *A23K 20/105* (2016.05); *A23K 20/158* (2016.05); *A23L 33/105* (2016.08); *A61K 31/19* (2013.01); *A61K 31/56* (2013.01); *A61K 36/88* (2013.01); *A61K 36/896* (2013.01); *A23V 2002/00* (2013.01); *A61K 2236/331* (2013.01)

(58) Field of Classification Search
CPC ....................................................... A61K 36/00
USPC ....................................................... 424/725
See application file for complete search history.

(56) References Cited

U.S. PATENT DOCUMENTS

| | | |
|---|---|---|
| 2006/0257386 A1 | 11/2006 | Zimmerman et al. |
| 2011/0076349 A1 | 3/2011 | Yoshihara et al. |
| 2012/0009163 A1* | 1/2012 | Sawada ............... A61K 35/744 424/93.44 |
| 2012/0183635 A1 | 7/2012 | De Saizieu et al. |
| 2013/0237716 A1 | 9/2013 | Gozu et al. |

FOREIGN PATENT DOCUMENTS

WO 20120142511 A2 10/2012

OTHER PUBLICATIONS

International Search Report and Written Opinion of corresponding PCT Serial No. PCT/US2014/065336 dated Jan. 29, 2015.

* cited by examiner

*Primary Examiner* — Michael V Meller
(74) *Attorney, Agent, or Firm* — Dinsmore & Shohl LLP

(57) ABSTRACT

Provided are process of regulating expression of one or more genes or proteins involved in circadian rhythm. A subject such as a cell is administered or contacted to an extract of rosemary, an extract of *hemerocallis fulva*, or combinations thereof, optionally provided as a component of a dietary supplement. The presence of one or more active agents in the extracts administered at a targeted administration time alters the expression of one or more genes or proteins involved in circadian rhythm, illustratively CLOCK, BMAL1, FBXL3, FBXL21, or SIRT1.

4 Claims, 5 Drawing Sheets

OGD:     CON  RE (20μg/mL)  HE (20μg/mL)  RE+HE (20μg/mL, each)

OGD: CON  RE (20μg/mL)  HE (20μg/mL)  RE+HE (20μg/mL, each)

OGD:   CON   RE (20μg/mL)   HE (20μg/mL)   RE+HE (20μg/mL, each)

OGD: CON   RE (20μg/mL)   HE (20μg/mL)   RE+HE (20μg/mL, each)

US 10,039,798 B2

EXTRACTS OF ROSEMARY OR HEMEROCALLIS FULVA AND METHODS OF USING SAME TO PROMOTE CIRCADIAN RHYTHM

CROSS REFERENCE TO RELATED APPLICATIONS

This application is the U.S. National Phase of PCT/US2014/065336, filed Nov. 13, 2014 and depends from and claims priority to U.S. Provisional Application No.: 61/903,434 filed Nov. 13, 2013, and U.S. Provisional Application No.: 61/903,440 filed Nov. 13, 2013, the entire contents of each of which are incorporated herein by reference.

FIELD OF THE INVENTION

The present invention relates to dietary supplement compositions containing rosemary or *Hemerocallis fulva* extracts and methods for promoting or maintaining or modulating protein expression or circadian rhythm.

BACKGROUND OF THE INVENTION

Living organisms from cyanobacteria to mammals display circadian rhythms (i.e., oscillations with 24-h periodicities) in multiple physiological and behavioral processes. These rhythms are found in nearly all living organisms. Circadian rhythms are generated endogenously and function under tightly regulated genetic control.

Circadian rhythms control a variety of biological processes, including sleep/wake cycles, body temperature, hormone secretion, gastrointestinal function, metabolic glucose homeostasis, and immunological functions. Biological clocks exhibiting circadian rhythms exist in virtually all tissues, with a series of clock genes generating the rhythm through protein feedback effects on their own synthesis.

These multiple endogenous clocks are distributed in every cell of the organism, which may result in each organ having its own timed circadian rhythm. A complex mechanism of activation and feedback regulate the expression, post-translational modification, translocation, and degradation of circadian proteins. The transcription factor CLOCK-BMAL1 is a core component of the molecular clock machinery that drives circadian gene expression and physiology in mammals. CLOCK and BMAL1 are each basic helix-loop-helix (bHLH) PAS-domain transcription factors that together form the positive elements of the central oscillatory loop. CLOCK and BMAL1 form a heterodimer that binds to E-box elements in the promoters of target genes. Some of the primary genes under transcriptional control by CLOCK:BMAL1 encode the three Period (mPer1, mPer2, and mPer3) proteins and two Cryptochromegenes (mCry1 and mCry2) proteins. Following translation of the Per and Cry proteins, they translocate to the nucleus where they act as potent inhibitors of CLOCK:BMAL1-induced gene transcription forming a negative feedback loop and regulating the rhythmic expression of many genes. The PERIOD protein mPER2, the gene of which is also under CLOCK:BMAL1 transcriptional control, functions as a stimulator of Bmal1 transcription, forming the positive feedback loop and enhancing CLOCK:BMAL1 activity. The regulation of these positive and negative feedback loops regulates the circadian rhythm within the cell.

SIRT1, a nicotinamide adenine dinucleotide-dependent sirtuin, has been shown to promote cell survival by inhibiting apoptosis or cellular senescence in mammalian cells. Recent studies have provided a link between the cellular metabolic function of SIRT1 and the circadian rhythm (controlled by the CLOCK:BMAL1 machinery) where it has been shown that SIRT1 controls circadian clock circuitry and promotes cell survival providing a connection with age-related neoplasms. Also, circadian function decays with aging in normal mice, and boosting their SIRT1 levels in the brain could prevent this decay. Conversely, loss of SIRT1 function impairs circadian control in young mice, mimicking what happens in normal aging. Moreover, SIRT1 has been shown to exert this control by regulating the genes BMAL1 and CLOCK, the two major keepers of the central circadian clock.

Oxygen and circadian rhythmicity are essential in a myriad of physiological processes to maintain homeostasis, from blood pressure and sleep/wake cycles, as well as in cellular signaling pathways that play critical roles in health and disease. Oxidative stress can induce the dysregulated circadian rhythms. Thus, there is a need for new compositions and methods for regulating proper protein expression and circadian rhythm.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Stresses can have a detrimental effect on many physiological regulatory systems. Among these are circadian rhythms. It was discovered that particular extracts of rosemary, *hemerocallis fulva*, the active portions or components thereof, or combinations thereof can restore expression of mediators of circadian rhythms in cells such as the proteins CLOCK, BMAL1, FBXL3, FBXL21, or SIRT1. This can beneficially effect physiological function and reduce the negative effects of stresses.

Provided are processes of altering an expression characteristic of a CLOCK, BMAL1, FBXL3, FBXL21, or SIRT1 protein in a subject including: administering to said subject an effective amount of an extract of rosemary, an extract of *hemerocallis fulva*, or combinations thereof at an administration time, said effective amount comprising ursolic acid at 10% or greater by weight; where the administering occurs at or between −4 hours to 12 hours after light exposure. In some aspects, the administration time occurs at or between 0 hours to 12 hours after light exposure, optionally at or between 1 hours to 3 hours after light exposure or 10-14 hours after light exposure, optionally at or between −4 hours to 0 hours prior to light exposure.

Provided are processes of altering an expression characteristic of a circadian rhythm protein in a subject including administering to said subject an effective amount of an extract of rosemary, an extract of *hemerocallis fulva*, an active portion or component thereof, or combinations thereof at an administration time, where the administration time occurs such that the extract, an active portion or component thereof, or combinations thereof contacts a cell having a circadian rhythm thereby increasing the expression of CLOCK, BMAL1, FBXL3, FBXL21, SIRT1, or combinations thereof in said cell.

In some aspects, an extract is a water extract. In some aspects, an extract is a component of a dietary supplement.

Administration is optionally once daily, twice daily, more frequently, or on an as needed basis. Administration optionally occurs at or between −4 hours to 12 hours after light exposure. In some aspects, the administration time occurs at or between 0 hours to 12 hours after light exposure, optionally at or between 1 hours to 3 hours after light exposure or 10-14 hours after light exposure, optionally at or between −4 hours to 0 hours prior to light exposure.

An extract in any of the processes optionally includes 10% or greater ursolic acid, optionally 25% or greater ursolic acid.

Also provided are processes of altering an expression characteristic of a circadian rhythm protein in a subject including administering to a subject, where the administration time occurs such that said ursolic acid contacts a cell having a circadian rhythm thereby increasing the expression of CLOCK, BMAL1, FBXL3, FBXL21, SIRT1, or combinations thereof in said subject. The ursolic acid is optionally obtained from extracting the ursolic acid from rosemary, *hemerocallis fulva*, or combinations thereof with water, an alcohol or combinations thereof. The ursolic acid is optionally administered once daily, twice daily, more frequently, or on an as needed basis. Administration optionally occurs at or between −4 hours to 12 hours after light exposure. In some aspects, the administration time occurs at or between 0 hours to 12 hours after light exposure, optionally at or between 1 hours to 3 hours after light exposure or 10-14 hours after light exposure, optionally at or between −4 hours to 0 hours prior to light exposure.

In any of the processes a subject is optionally in need of improved expression of a circadian rhythm gene or protein, optionally due to exposure to a stress or other environmental condition that reduces expression of a circadian rhythm gene or protein such as CLOCK, BMAL1, FBXL3, FBXL21, SIRT1, or combinations thereof.

DETAILED DESCRIPTION OF ASPECTS OF THE INVENTION

Figure 1A:
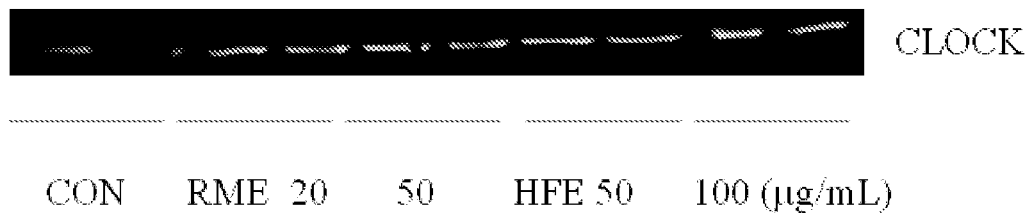
FIG. 1A illustrates the effects of RME and HFE on CLOCK protein expression in C6 cells.

The following description of particular aspect(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes or compositions are described as an order of individual steps or using specific materials, it is appreciated that steps or materials may be interchangeable such that the description of the invention may include multiple parts or steps arranged in many ways as is readily appreciated by one of skill in the art.

Provided are processes for altering a circadian rhythm in a subject. Altering a circadian rhythm is understood as altering, optionally increasing, the expression level, post-translational modification state, nuclear or cytoplasmic location or translocation, or RNA expression rate of a protein normally involved in a 24-hour or other regular cycle in one or more cell types in a subject. A process includes administering to a subject an effective amount of an extract of rosemary (RME), an extract of *hemerocallis fulva* (HFE), active portion or component thereof, or combinations thereof or a dietary supplement containing in whole or in part of an extract of rosemary, an extract of *hemerocallis fulva*, active portion or component thereof, or combinations thereof. Such an administration is at an administration time. The administration of the extract of rosemary, an extract of *hemerocallis fulva*, active portion thereof, or combinations thereof or a dietary supplement containing such will alter an expression characteristic of a protein of CLOCK, BMAL1, FBXL3, FBXl21, SIRT1, or combinations thereof in the subject. As such, the invention has utility for altering or adjusting one or more expression characteristics of a protein involved in a circadian rhythm in a cell.

An "expression characteristic" is the transcription of a gene encoding a circadian rhythm protein, translation of RNA encoding a circadian rhythm protein, localization of RNA encoding a circadian rhythm protein, protein function, protein localization, protein post-translational modification, or other parameter recognized in the art related to protein expression and function.

The invention provides materials in the form of botanical extracts, such as an extract of rosemary, an extract of *hemerocallis fulva*, active portion thereof, or combinations thereof, alone or as part of a dietary supplement that have utility for altering one or more expression characteristics of a protein involved in a circadian rhythm in a subject. The extract, active portion thereof, or dietary supplement may be in pharmaceutical dietary supplement composition in solid, semi-solid, or liquid dosage forms, such as, for example, tablets, chewables, suppositories, pills, capsules, powders, liquids, or suspensions, and may be provided in unit dosages suitable for a single administration. Time release preparations are also contemplated as effective dosage formulations. The compositions may include an effective amount of a selected extract of rosemary, *hemerocallis fulva*, active portion thereof, or combinations, optionally in combination with a pharmaceutically acceptable carrier and, in addition, may include other medicinal agents, pharmaceutical agents, carriers, or diluents.

The extracts are recognized to include an active ingredient as an active portion of an extract, or the sole portion of an extract. "Active ingredient" refers a component present in the extract that renders, directly or indirectly, the intended effect of the extract. In some aspects, an active ingredient is ursolic acid. Extraction parameters such as water quality, heating temperature, drying temperature, heating time, drying time, and filtering processes all contribute to the quality and efficiency of the process. Water quality directly affects the concentration of active ingredient(s). Poor quality water may cause active ingredient(s) to become decomposed or oxidized during or following the extraction process.

The rosemary or *hemerocallis fulva* may be obtained from various resources. Rosemary, or *Rosmarinus officinalis*, is a woody bush native to the Mediterranean region. Extracts of rosemary may be made from *Rosmarinus* spp. and preferably from the leaves and young flowering tops of fresh rosemary (*Rosmarinus officinalis* L. and its cultivars). Rosemary extraction may be performed by harvesting the leaves of a rosemary plant and reducing them in size such as by chopping to improve solvent penetration. A typical particle size is optionally 0.5-5.0 mm, or any value or range therebetween. In some aspects, the leaf is chopped into a powder type substance with a particle size of less than 0.5 mm. The chopped plant material is combined with a suitable extraction solvent such as water and/or a low molecular weight alcohol (e.g. $C_4$-$C_6$ alcohol) such as ethanol. The plant material is combined with the solvent for an extraction time of 18 to 36 hours. The extraction temperature is optionally the range 10° C. to 45° C. The resulting extract liquid is separated from the solid material and filtered, optionally with a sterile filter. Optionally, the resulting extract is poured onto nonstick tray and allowed to dry at 80-90° C. Vacuum-spray dry equipment is optionally used for the drying procedure. The resulting dry extract powder is weighed. An extraction ratio is calculated as w/20×100% with w as the weight (g) of the dry extract powder. The sample and water ratio, heat time, volume of water in the second extraction may vary depending on the amount of the raw material used for extraction.

Extracts of *Hemerocallis fulva* are optionally obtained from extraction in an extraction solvent such as water and/or low molecular weight alcohol such as ethanol. Extracts are prepared from plants belonging to the genus *Hemerocallis* of the family Liliaceae of the order Liliales are used. Examples of such plants include Akinowasuregusa (*Hemerocallis fulva* L. *sempervirens* M. Hotta or *Hemerocallis sempervirens* Araki), Honkanzo (*Hemerocallis fulva* L. var. *fulva*), Nokanzo (*Hemerocallis fulva* L. var. *longituba* Maxim or *Hemerocallis longituba* Miq.), and Yabukanzo (*Hemerocallis fulva* L. var. *kwanso* Regal). An extract is optionally prepared from whole plants or plant parts, such as leaves, stems, and roots.

In some aspects, an extract is prepared by drying the plant material and optionally cutting the material into a suitable size for extraction, such as the sizes described for rosemary. The plant material is combined with an extraction solvent (e.g. water, aqueous buffer, low molecular weight alcohol, or combinations thereof) that is preheated to a temperature of 60° C. to 100° C. for an extraction time, typically of 20 to 90 minutes. The particulate material is then removed by gravity separation, centrifugation, or filtering, optionally with a filter size suitable for aseptic filtration. The resulting extract is optionally poured onto nonstick tray and allowed to dry at 80-90° C. Vacuum-spray dry equipment is optionally used for the drying procedure. The resulting dry extract powder is weighed. An extraction ratio is calculated as w/20×100% with w as the weight (g) of the dry extract powder. The sample and water ratio, heat time, volume of water in the extraction may vary depending on the amount of the raw material used for extraction.

In some aspects, a second extraction of either plant material is performed optionally using the same extraction parameters or differing extraction parameters. Optionally, a second extraction is performed in a low molecular weight alcohol optionally of $C_2$-$C_4$. The first and second extraction solutions are optionally combined together and dried.

In some aspects, an extract includes or consists of ursolic acid as an active ingredient. Ursolic acid is optionally present in an extract at a concentration of 10 weight percent or greater. In some aspects, ursolic acid is present in an extract at a concentration of 25 weight percent or greater. Optionally, ursolic acid is present at a weight percent at or in excess of 5, 10, 15, 20, 25, 30, 35, 40, 45, 50, 55, 60, 65, 70, 75, 80, 85, 90, 95, 96, 97, 98, 99, 99.1, 99.2, 99.3, 99.4, 99.5, 99.6, 99.7, 99.8, or 99.9.

While ursolic acid is described as a component of or the product representing an extract, it is appreciated that the term "extract" may in some aspects include otherwise isolated, purified, or chemically synthesized ursolic acid. As such, an "extract" is in some aspects ursolic acid obtained either by extraction from a natural or non-natural source, or used as a chemically synthesized ursolic acid.

Depending on the intended mode of administration, the extract can be in pharmaceutical compositions in the form of solid, semi-solid or liquid dosage forms, such as, for example, tablets, suppositories, pills, capsules, powders, liquids, or suspensions, and may be provided in unit dosages suitable for a single administration. Time release preparations are specifically contemplated as effective dosage formulations. The compositions will include an effective amount of the selected extract in combination with a pharmaceutically acceptable carrier and, in addition, may include other medicinal agents, pharmaceutical agents, carriers, or diluents.

In a solid composition aspect, conventional nontoxic solid carriers may include, for example, pharmaceutical grades of mannitol, lactose, starch, magnesium stearate, sodium saccharine, talc, cellulose, glucose, sucrose and magnesium carbonate. Liquid pharmaceutically administrable compositions may, for example, be prepared by dissolving or dispersing an active compound with optimal pharmaceutical adjuvants in an excipient, such as water, saline, aqueous dextrose, glycerol, or ethanol, to form a solution or suspension. For example, the pharmaceutical composition may contain minor amounts of nontoxic auxiliary substances such as wetting or emulsifying agents, pH buffering agents, for example, sodium acetate or triethanolamine oleate. Actual methods of preparing such dosage forms are known, or will be apparent, to those skilled in this art; for example, see Remington's The Science and Practice of Pharmacy (20$^{th}$ Edition).

In oral administration aspects, fine powders or granules of extract, or a liquid extract may contain diluting, dispersing, or surface active agents. The extract may be presented in water or in syrup, in capsules or sachets in the dry state, or in a non-aqueous solution or suspension. Suspending agents may also be included in tablets, which may include binders and lubricants in a suspension. Flavoring, preserving, suspending, thickening, or emulsifying agents may be also included to modify the taste and texture of the composition. The tablets and granules provided for oral administration may further be coated for ease of digestion.

In some aspects, the extract containing dietary supplement composition may be combined with one or more other active agents. An active agent optionally functions synergistically with an extract material. Active agents illustratively include vitamins (such as vitamin A, vitamin B, vitamin C, vitamin D, vitamin E or vitamin K), antioxidants (such as acai, wolfberry, alpha lipoic acid, astazanthin, or fucoxanthin), or other regulators of one or more circadian rhythm protein (illustratively resveratrol or polygonum), or any combination of the above. The extract according to the present invention is available as a food additive thereto. Examples include foods in a liquid, semi-liquid, solid, paste, or jelly form.

Processes are provided for altering an expression characteristic of a circadian rhythm protein in a subject. As used herein, a subject is defined as an organism (such as a human, non-human primate, equine, bovine, murine, or other mammal), or a cell. Illustrative examples of cells include neuronal cells, muscle cells, or any other cell that endogenously or exogenously expresses a circadian rhythm protein.

The inventors unexpectedly discovered that administration of an extract of rosemary, an extract of *hemerocallis fulva*, or combinations thereof will alter one or more expression characteristics of a circadian rhythm protein. Circadian rhythm protein expression is altered when a cell is contacted by an extract of rosemary, an extract of *hemerocallis fulva*, or combinations thereof. Illustrative examples of proteins include the proteins CLOCK, BMAL1, FBXL3, FBXl21, SIRT1.

The Circadian Locomotor Output Cycles Kaput (CLOCK) protein is optionally altered in one or more expression characteristics in aspects of the invention. Optionally CLOCK protein expression in the cytoplasm or levels in the nucleus following translocation are increased in the inventive processes. Optionally, an extract is an extract of rosemary that increases expression of a CLOCK protein. Optionally, an extract is an extract of *hemerocallis fulva* that increases expression of a CLOCK protein. Contacting a cell with an extract of rosemary, an extract of *hemerocallis fulva*, or combinations thereof is shown to increase the expression of CLOCK protein within 2 hours of administration. Illustratively, CLOCK protein expression is enhanced (e.g. increased) by a value of 5% to 300% or more, or any value or range therebetween. Optionally, CLOCK protein expression is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

Brain and muscle Arnt-like protein-1 (BMAL1; also known as MOP3 or Arnt3) is a transcription factor known to regulate circadian rhythm. Optionally BMAL1 protein expression in the cytoplasm or levels in the nucleus following translocation are increased in the inventive processes. Optionally, an extract is an extract of rosemary that increases expression of a BMAL1 protein. Optionally, an extract is an extract of *hemerocallis fulva* that increases expression of a BMAL1 protein. Contacting a cell with an extract of rosemary, an extract of *hemerocallis fulva*, or combinations thereof is shown to increase the expression of BMAL1 protein within 2 hours of administration. Illustratively, BMAL1 protein expression is enhanced (e.g. increased) by a value of 5% to 300% or more, or any value or range therebetween. Optionally, BMAL1 protein expression is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

F-box/LRR-repeat protein 3 (FBXL3) is a member of the F-box protein family that functions in phosphorylation-dependent ubiquitination. Optionally FBXL3 protein expression in the cytoplasm or levels in the nucleus following translocation are increased in the inventive processes. Optionally, an extract is an extract of rosemary that increases expression of a FBXL3 protein. Optionally, an extract is an extract of *hemerocallis fulva* that increases expression of a FBXL3 protein. Contacting a cell with an extract of rosemary, an extract of *hemerocallis fulva*, or combinations thereof is shown to increase the expression of FBXL3 protein within 2 hours of administration. Illustratively, FBXL3 protein expression is enhanced (e.g. increased) by a value of 5% to 300% or more, or any value or range therebetween. Optionally, FBXL3 protein expression is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

F-box/LRR-repeat protein 21 (FBXL21) is a member of the F-box protein family that functions in phosphorylation-dependent ubiquitination. Optionally FBXL21 protein expression in the cytoplasm or levels in the nucleus following translocation are increased in the inventive processes. Optionally, an extract is an extract of rosemary that increases expression of a FBXL21 protein. Optionally, an extract is an extract of *hemerocallis fulva* that increases expression of a FBXL21 protein. Contacting a cell with an extract of rosemary, an extract of *hemerocallis fulva*, or combinations thereof is shown to increase the expression of FBXL21 protein within 2 hours of administration. Illustratively, FBXL21 protein expression is enhanced (e.g. increased) by a value of 5% to 300% or more, or any value or range therebetween. Optionally, FBXL21 protein expression is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

Sirtuin 1 (silent mating type information regulation 2 homolog 1) (SIRT1) is a protein involved in deacetylation of proteins that contribute to cellular regulation. Optionally SIRT1 protein expression in the cytoplasm or levels in the nucleus following translocation are increased in the inventive processes. Optionally, an extract is an extract of rosemary that increases expression of a SIRT1 protein. Optionally, an extract is an extract of *hemerocallis fulva* that increases expression of a SIRT1 protein. Contacting a cell with an extract of rosemary, an extract of *hemerocallis fulva*, or combinations thereof is shown to increase the expression of SIRT1 protein within 2 hours of administration. Illustratively, SIRT1 protein expression is enhanced (e.g. increased) by a value of 5% to 300% or more, or any value or range therebetween. Optionally, SIRT1 protein expression is enhanced by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more.

Detecting and optionally quantifying circadian protein expression is achieved by any of many methods known in the art. Illustratively, circadian protein expression is detected and optionally quantified by enzyme linked immunosorbent assay (ELISA), mass spectrometry, western blot, gel electrophoresis optionally coupled with staining such as by Coomassie brilliant blue or silver stain, or by target specific stains, flow cytometry, immunoprecipitation, or by other method known in the art. In some aspects, an ELISA is used to detect and optionally quantify circadian protein expression. For example, ELISA kits for SIRT1 and SIRT2 are available from Enzo Lifesciences, Plymouth Meeting, Pa. Kits for other sirtuins are similarly available from commercial sources. Antibodies directed to CLOCK, BMAL1, and SIRT proteins suitable for use in ELISA, western blot, immunofluorescence or other applications are available from Santa Cruz Biotechnology, Santa Cruz, CA. Anti-FBXL21 and anti-FBXL3 antibodies are available from abcam, Cambridge, Mass.

A process optionally includes administration of an extract or dietary supplement containing extract at an administration time. Administration is optionally once daily, twice daily or more. Administration optionally is done 1, 2, 3, 4 or more times each day. Optionally, administration is done on an as needed basis. Optionally irregularly, or weekly. Optionally, administration is done once or twice weekly such as when a subject is transitioning from one schedule to another such as due to travel, shift work, weekend to work schedule or work to weekend schedule, or other necessary time. Optionally, an administration time is following exercise. Optionally, an administration time when one or more symptoms of a disease or condition are present, or conditions exist that such a symptom is expected or may occur. Optionally, administration is prior to, following, during, or in lieu of a meal, snack or other consumption of food or nutritious drink. Optionally, administration is prior to, during or following the consumption of alcohol. Optionally, an administration time is at the initiation of a work period.

Administration time is optionally from −4 hours to 12 hours following light exposure. Optionally, administration is from 0 to 12 hours after light exposure. Optionally, an administration time is upon waking independent of the time of day or the onset of light exposure. Optionally, an administration time is in the evening. The inventors have shown that administration of an effective amount of an extract of rosemary, an extract of *hemerocallis fulva*, or combinations thereof increases the expression of several proteins involved in several circadian processes. An administration time may be tailored to a desired time to have expression of such a protein or collection of proteins expressed to adjust the sleep-wake cycle of a subject, or to improve wakefulness at a desired time with the improvement in wakefulness optionally, not due to improved rest.

In a typical regimen, the extract materials are taken orally between one and three times daily, or on an as needed basis; although, other routes of administration may be utilized. Also, it should be noted that the extracts of the present invention may be utilized in the form of derivatives. For example, the extracts may be bonded, chemically or physically, to other species and moieties such as synthetic polymers, liposomes, small organic molecules, chitin, chitosan, other biopolymers and the like. In view of the teaching presented herein, still further combinations will be readily apparent to those of skill in the art.

A subject is administered a composition in a dosage so that each dose of the extract supplement selected to deliver an amount of active agent suitable to have an effect on an expression characteristic of a circadian protein. Variable dosing regimens are operative. While in some instances, a single dose treatment may be effective in producing therapeutic effects, in other instances a treatment period in the range of, for example, six weeks to three or six months or more may be utilized. The composition may be administered orally, parentally, or intravenously, intramuscularly, intraperitoneally, by transdermal injection, or by contact with a cell or tissue such as by immersion or other form of contact. Injectables may be prepared in conventional forms, either liquid solutions or suspensions, solid forms suitable for solution or prior to injection, or as suspension in liquid prior to injection or as emulsions.

The dose of the composition may vary depending on the age, weight, general condition of the subject. For example, dosage is in the range of 1-1,000 mg of equivalent of dry extract powder extract per day may be an effective range. In some aspects, a dosage is between 10 and 800 mg per day, optionally from 100 to 600 mg per day, optionally 200-400 mg per day, optionally 400 mg per day. Dosage is optionally 1, 2, 3, 4, or more times daily. Optionally, dosage is twice daily. Optionally, dosage is 200 mg twice daily. The extract may also comprise 0.01%-100% of the dry weight of the composition. For example, a dietary supplement composition may comprise 20%-50% of the dry weight of the extract composition. An "effective amount" is defined as that capable of altering one or more expression characteristics of a circadian protein or a gene encoding a circadian protein relative to a control.

An extract optionally is or is a part of a dietary supplement composition. An extract is optionally present in a dietary supplement composition at 10%-100% by weight, optionally 20%-50% by weight, optionally 30%-40% by weight, or any value or range between 10% and 100% of the dry weight of the dietary supplement composition.

Various aspects of the present invention are illustrated by the following non-limiting examples. The examples are for illustrative purposes and are not a limitation on any practice of the present invention. It will be understood that variations and modifications can be made without departing from the spirit and scope of the invention.

EXPERIMENTAL

It was investigated whether an extract of rosemary (RME) and an extract of *hemerocallis fulva* (HFE) regulate key circadian protein expression in normal rat C6 glioma cells and IPEC-1 (Porcine intestinal epithelial cell lines), using immunofluorescence and western blotting analyses. Oxygen and circadian rhythmicity are essential in a myriad of physiological processes to maintain homeostasis, from blood pressure and sleep/wake cycles, down to cellular signaling pathways that play critical roles in health and disease. Oxidative stress can induce the dysregulated circadian rhythms. We also test if RME and HFE attenuate the damages of these proteins expression from oxygen-glucose deprivation (OGD).

The dried rosemary extract and *Hemerocallis fulva* extract were provided by Integrity Nutraceuticals International (Spring Hill, Tenn., USA). The dried powder of each extract contains 25% ursolic acid. To obtain a more pure extract fraction, the dried rosemary or *Hemerocallis fulva* powder (1 g) was incubated with an aqueous phosphate buffer solution 0.01 M, pH 7.4 (5 mL), at 60° C. for 4 hours, then centrifuged at 6000 rpm for 15 minutes. The supernatant was filtrated by 40 μm filter mesh and saved for the concentration evaluation. Aliquots of RME and HFE were prepared at 10 mg/mL and stored at −20° C. for use in subsequent studies.

C6 glioma cells (CCL-107) were purchased from American Type Culture Collection (ATCC; Manassas, Va.). Cell cultures were grown in F-12 K medium (Gibco/Invitrogen) supplemented with 10% horse serum and 2% fetal bovine serum and maintained at 37° C. with 5% $CO_2$/95% air. Cultures were grown to 85% confluency in 75 mm flasks and, after trypsinization, were seeded in 35 mm culture dishes or 6 well plates; and grown to confluence during the experimental period. All cultures were used in the experiments between passages 22 and 32. Plated cells were grown for 2 days before treatment with an extract or control.

Culture of IPEC-1 cells was carried out at 37° C. in an atmosphere containing 5% $CO_2$. Undifferentiated IPEC-1 cells were maintained in serial passage in growth medium (GM): DMEM/F12 medium supplemented with 5% FBS, insulin, transferrin (ITS Premix), epidermal growth factor, penicillin and streptomycin. Cells were maintained in serum-containing GM for 48 h for the experiments.

The effects of the RME or HFE were studied in cells by staining for target proteins using the following primary antibodies all provided by Abcam Inc, Cambridge, Mass. SIRT1 was detected by ab110304 Mouse monoclonal [19A7AB4]. KAT13D/CLOCK was detected using ab134165 Rabbit monoclonal [EPR6227]. BMAL1 was detected using the C-terminal recognizing antibody ab140646 Rabbit monoclonal [EPR8355(2)]. FBXL3 was detected using ab96645 Rabbit polyclonal. FBXL21 was detected using ab57302 Mouse monoclonal. For each immunofluorescence study the cells were stained with the primary antibody for the target of interest followed by incubation with AlexaFluor® 594-conjugated normal rabbit IgG (green) or AlexaFluor® 488-conjugated normal mouse IgG (red).

C6 cells were treated with saline with or without RME (20, 50 and 100 μg/mL) or without HFE (50, 100 and 200 μg/mL) in the medium for 2 h at 37° C. The effects of rosemary extract (RME) and *hemerocallis fulva* extract (HFE) on circadian locomoter output cycles protein kaput (CLOCK) protein expression in C6 glioma cells are determined by immunofluorescence. A 2h treatment with RME or HFE significantly induced increased the intensity of immunofluorescence of CLOCK compared with the controls indicating enhanced CLOCK protein expression.

Similar results of RME and HFE on CLOCK protein expression were observed in IPEC-1 cells. IPEC-1 cells were treated with saline with or without RME (20, 50 and 100 μg/mL) or with or without HFE (50, 100 and 200 μg/mL) in the medium for 6 h at 37° C. 6 h RME and HFE treatment significantly induced the intensity of immunofluorescence of CLOCK compared with the controls.

Figure 1B:
FIG. 1B illustrates the effects of RME and HFE on CLOCK protein expression in C6 cells.

FIG. 1 illustrates the effects of RME and HFE on CLOCK (FIG. 1A) and BMAL1 (FIG. 1B) protein expression in C6 cells. C6 cells were treated with saline with or without RME (20 and 50 μg/mL) or with or without HFE (50 and 100 μg/mL) in the medium for 7 h at 37° C. Representative immunoblots show increased expression in RME and HFE treated C6 cells.

Oxygen glucose deprivation (OGD) was induced in cultures as described by Panickar et al. (Panickar et al., 2009a). Briefly, cultures were washed twice with a balanced salt solution (BSS) with the following composition (in mM): NaCl 116, KCl 5.4, $CaCl_2$ 1.8, $MgSO_4$ 0.8, $NaH_2PO_4$ 0.83, $NaHCO_3$ 24 and phenol red 0.001 w/v; pH 7.4. Following washes, BSS was added to the cultures and placed in an airtight container (Billups chamber; Billups-Rothenberg Inc., Del Mar, Calif.) and continuously flushed with 95% $N_2$/5% $CO_2$ for 5 hr. Following the OGD, BSS was removed and normal media was added immediately afterwards.

Oxygen-glucose deprivation (OGD)-induced decreased CLOCK expression is reversed and further enhanced by RME and HFE in IPEC-1 cells. The RME and HFE were added to the media during 4 hr OGD and added to normal media for other 3 hr, immediately after the end of 4 hr OGD at 37° C. Sample photomicrographs of CLOCK fluorescence after 4 hr OGD and 3 h reperfusion in normal control (CON), OGD, and OGD+two dosages RME or HFE 100 μg/ml or 200 μg/ml illustrate increases in CLOCK expression relative to control and OGD treated cells.

Immunofluorescence measurements demonstrated that RME and HFE each increased FBXL3 protein levels in 4 hr oxygen-glucose deprivation (OGD) and 2 hr reperfusion treated C6 glioma cells. The RME or HFE were added to the media during 4 hr OGD and added to normal media for other 2 hr, immediately after the end of 4 hr OGD at 37° C. Sample photomicrographs of FBXL3 fluorescence after 4 hr OGD and 2 h reperfusion in OGD, and OGD+two dosages RME and HFE 50 μg/ml or 100 μg/ml illustrate enhanced expression of FBXL3 due to the presence of the extract.

RME (A) and HFE (B) both increased FBXL3 protein levels in 4 hr oxygen-glucose deprivation (OGD) and 2 hr reperfusion treated IPEC-1 cells as illustrated by immunofluorescence. The RME and HFE were added to the media during 4 hr OGD and added to normal media for other 3 hr, immediately after the end of 4 hr OGD at 37° C. Sample photomicrographs of FBXL3 fluorescence after 4 hr OGD and 3 h reperfusion in OGD, and OGD+RME or HFE at either 50 μg/ml or 100 μg/ml demonstrate enhanced expression of FBXL3 protein due to extract exposure.

Figure 2A:
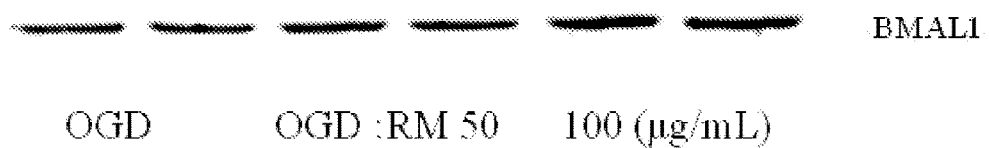
FIG. 2A illustrates RME increased BMAL1 protein levels in 4 hr oxygen-glucose deprivation (OGD) and 2 hr reperfusion treated C6 cells.
Figure 2B:
FIG. 2B illustrates RME increased FBXL21 protein levels in 4 hr oxygen-glucose deprivation (OGD) and 2 hr reperfusion treated C6 cells.

FIG. 2 illustrates RME increased BMAL1 (A) and FBXL21 (B) protein levels in 4 hr oxygen-glucose deprivation (OGD) and 2 hr reperfusion treated C6 cells. The RME was added to the media during 4 hr OGD and added to normal media for other 2 hr, immediately after the end of 4 hr OGD at 37° C. The blot bands are detected by Odyssey® Western Blotting. Briefly, the blot was probed with rabbit anti-BMAL1 or mouse anti-FBXl21 followed by detection with IRDye® 800CW Goat anti-Rabbit IgG (LI-COR P/N 926-32231) or IRDye 680RD Goat anti-Mouse IgG (LI-COR P/N 926-68070). Sample photomicrographs of FBXL21 fluorescence after 4 hr OGD and 2 h reperfusion in OGD, and OGD+two dosages RME are illustrated.

The effects of RME or HFE on SIRT1 protein expression in 4 hr oxygen-glucose deprivation (OGD) and 2 hr reperfusion treated C6 cells were examined by immunofluorescence. The RME or HFE were added to the media during 4 hr OGD and added to normal media for other 2 hr, immediately after the end of OGD at 37° C. SIRT1 fluorescence was increased in RME and HFE at either 50 μg/ml or 100 μg/ml in 4 hr OGD and 2 hr reperfusion treated C6 cells.

Rat L-6 myogenic cell line (ATCC) were grown as a monolayer in DMEM with 10% fetal bovine serum (FBS) at 37° C. in a humidified incubator with 5% $CO_2$. L-6 cells ($0.5 \times 10^6$) were seeded on 6-well plates. Experiments were initiated 48 hr after plating. For oxygen-glucose deprivation (OGD) of the L-6 cells, the culture media was replaced with hypoglycemic media and placed in an airtight Billups chamber and flushed with 95% $N_2$/5% $CO_2$ for 4 hr. Following OGD treatment, hypoglycemic media was replaced with regular media and returned to the incubator, with or without RME, HFE or the mixture of RME/HFE for 20 hr. After treatment, the cells were washed twice with cold PBS, and harvested by scraping in 200 μl of lysis buffer. Eighty micrograms of protein, which was determined by Bradford assay (Bio-Rad protein assay kit) was separated electrophoretically using a 10% sodium dodecyl sulfatepolyacrylamide gel electrophoresis gel and transferred to a nitrocellulose membrane. The membrane was incubated at room temperature in Odyssey blocking buffer including 0.05% Tween-20 containing primary antibodies as above directed to one of the following: SIRT1 (1:500), CLOCK (1:2000), Bmal1 (1:1000), or β-actin (1:1000). After washing with TBS-T three times, the membrane was incubated with anti-mouse or rabbit IRDye secondary antibodies (1:10,000) for 1 h at room temperature. Quantitative IR western blot detection was performed with Odyssey CLx Imager. Data were analyzed by one-way analysis of variance followed by post-hoc analysis of between group mean differences by Fisher's Least Significant Difference (LSD) test. Different superscripts indicate significant differences among groups ($p < 0.05$).

Figure 3A:
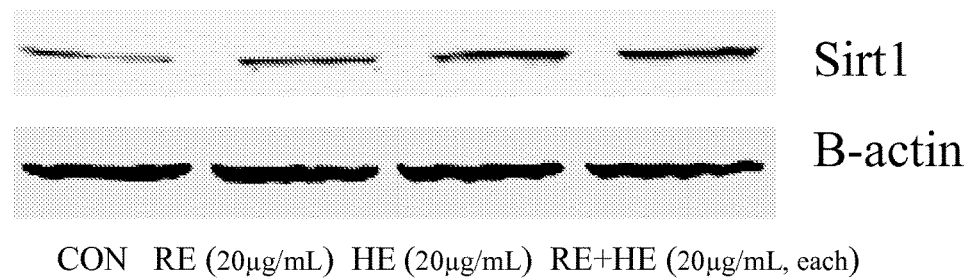
FIG. 3A illustrates SIRT1 levels increased in OGD Rat L-6 cells treated with RME, HFE, or both.
Figure 3B:
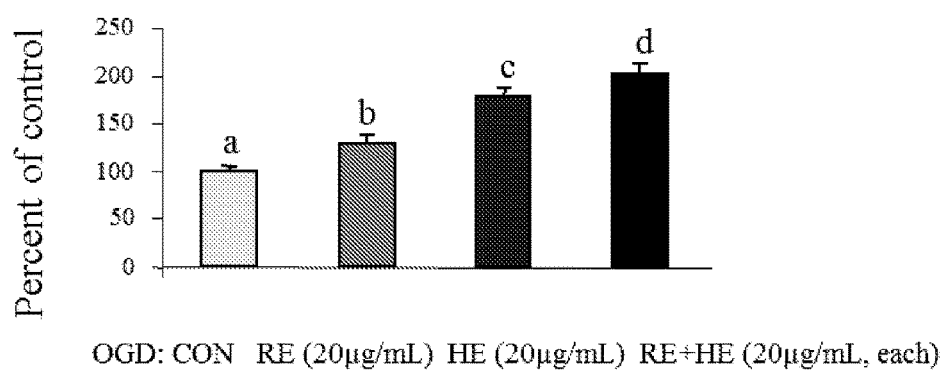
FIG. 3B illustrates quantifiable increases in SIRT1 levels in OGD treated Rat L-6 cells.

As illustrated in FIG. 3A, SIRT1 levels are increased in OGD treated L-6 cells by RME and/or HFE. The quantified amounts of protein are illustrated in FIG. 3B demonstrating significantly increased amounts of SIRT1 levels relative to control. An additional effect is observed in RME+HFE mixture treated cells on SIRT1 expression, compared with individual RME or HFE only treated cells.

Figure 4A:
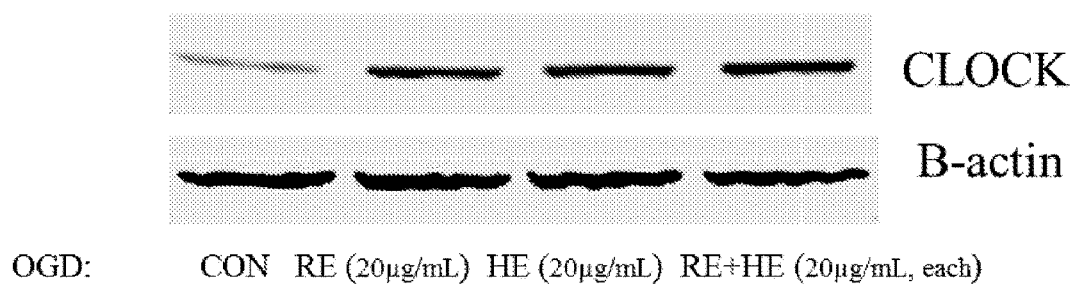
FIG. 4A illustrates CLOCK protein levels increased in OGD Rat L-6 cells treated with RME, HFE, or both.
Figure 4B:
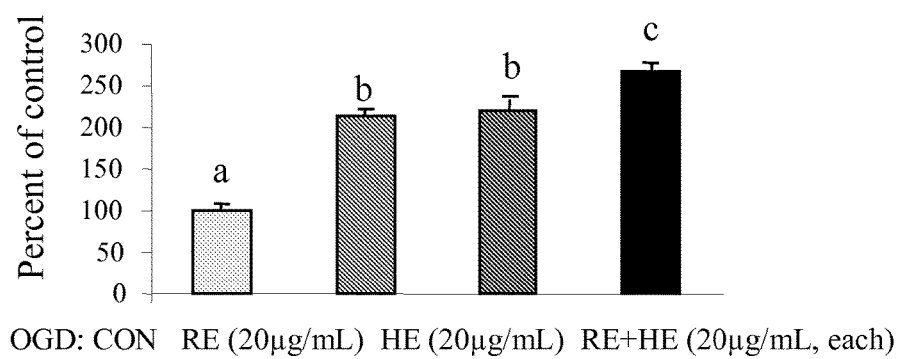
FIG. 4B illustrates quantifiable increases in CLOCK levels in OGD treated Rat L-6 cells by RME, HFE, or both.

FIG. 4 illustrates CLOCK protein levels increased in OGD treated L-6 cells by RME and/or HFE. RME, HFE, or both significantly enhance CLOCK protein expression in OGD treated L6 skeletal muscle cells. An additional effect in RME+HFE mixture treated cells on CLOCK expression is also observed compared to individual RME or HFE only treated cells.

Figure 5A:
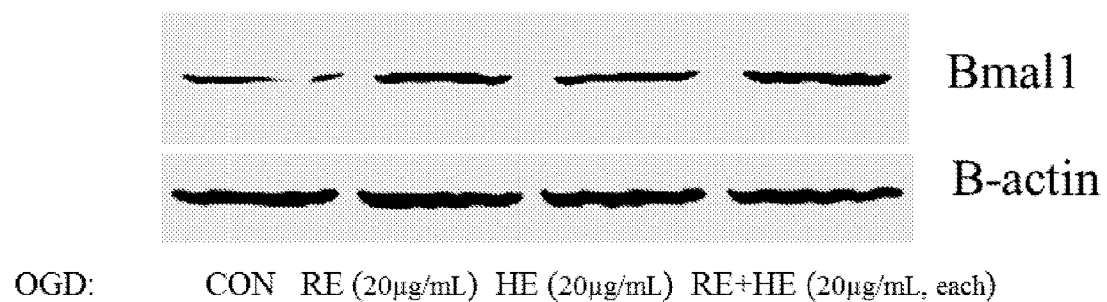
FIG. 5A illustrates Bmal1 protein levels increased in OGD Rat L-6 cells treated with RME, HFE, or both.
Figure 5B:
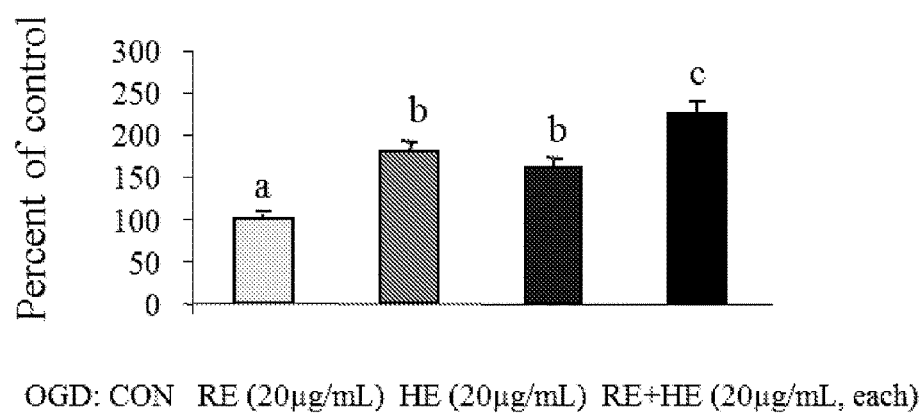
FIG. 5B illustrates quantifiable increases in Bmal1 levels in OGD treated Rat L-6 cells by RME, HFE, or both.

FIG. 5 illustrates Bmal1 protein levels increased in OGD treated L-6 cells by RME and/or HFE. RME, HFE, or both significantly enhance Bmal1 protein expression in OGD treated L-6 skeletal muscle cells. An additional effect is observed in cells treated with the RME+HFE compared with individual RME or HFE only treated cells.

Overall, a method for regulating expression of five key proteins linked to circadian rhythm disorders (CLOCK, BMAL1, FBXL3, FBXL21 and SIRT1) is described characterized by modulating expression in normal conditions and oxidative stress conditions in Rat Cr brain glioma cells, Rat L-6 myogenic cells, and IPEC-2 cells. Both extracts, RME and HFE, each significantly modulate the expression of circadian clock proteins in all cell types, and reverse cell damages identified by redcutions of the key proteins related to circadian rhythms induced by oxidative stress. These results indicate that RME and HFE extracts are useful as a new approach to attenuate the disruption of circadian rhythms, or to modulate circadian rhythm in a subject.

Ursolic Acid Enhances the Expression of Circadian Rhythm Proteins iPEC-1 cells were grown as a monolayer in DMEM with 10% fetal bovine serum (FBS) and the necessary supplements at 37° C. in a humidified incubator with 5% $CO_2$. iPEC1 cells were seeded on 35 mm dishes. Experiments were initiated 48 hr after plating. Cells were treated with saline or with ursolic acid at three separate dosages (1 µM; 5 µM; or 20 µM) in the medium for 24 hr at 37° C. The cells were then washed with ice-cold PBS and fixed with 4% paraformaldehyde for 10 min at room temperature followed by permeabilization with 0.3% Triton X-100 for 10 min. After being washed with PBS three times, cells were incubated for 1 hr in PBS containing 10% normal goat serum blocking solution. The cells were subjected to immunofluorescence staining with the target specific antibodies (SIRT1, CLOCK and Bmal1) overnight at 4° C. The cells were then washed with cold PBS three times for 3 min each, and incubated with Alexa-labeled secondary antibodies (Invitrogen) at room temperature for 1 h. The cells were examined by fluorescence microscopy (a Nikon TE2000-S microscope, Nikon, Tokyo, Japan).

24 hour incubation with ursolic acid significantly induced the intensity of immunofluorescence of SIRT1, CLOCK and Bmal1 compared with controls at all three concentrations of ursolic acid tested as evidenced by immunofluorescence staining.

Scientific and technical terms used herein are intended to have the meanings commonly understood by those of ordinary skill in the art. Such terms are found defined and used in context in various standard references illustratively including J. Sambrook and D.W. Russell, Molecular Cloning: A Laboratory Manual, Cold Spring Harbor Laboratory Press; 3rd Ed., 2001; F.M. Ausubel, Ed., Short Protocols in Molecular Biology, Current Protocols; 5th Ed., 2002; B. Alberts et al., Molecular Biology of the Cell, 4th Ed., Garland, 2002; D.L. Nelson and M.M. Cox, Lehninger Principles of Biochemistry, 4th Ed., W.H. Freeman & Company, 2004; Wild, D., The Immunoassay Handbook, 3rd Ed., Elsevier Science, 2005; Gosling, J. P., Immunoassays: A Practical Approach, Practical Approach Series, Oxford University Press, 2005; Antibody Engineering, Kontermann, R. and Dübel, S. (Eds.), Springer, 2001; Harlow, E. and Lane, D., Antibodies: A Laboratory Manual, Cold Spring Harbor Laboratory Press, 1988; Ausubel, F. et al., (Eds.), Short Protocols in Molecular Biology, Wiley, 2002; J. D. Pound (Ed.) Immunochemical Protocols, Methods in Molecular Biology, Humana Press; 2nd ed., 1998; B.K.C. Lo (Ed.), Antibody Engineering: Methods and Protocols, Methods in Molecular Biology, Humana Press, 2003; and Kohler, G. and Milstein, C., Nature, 256:495-497 (1975); the contents of each of which are incorporated herein by reference.

Methods involving conventional biological techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

REFERENCES

1. Schulz P, Steimer T: Neurobiology of circadian systems. CNS. Drugs 23 Suppl 2:3-13, 2009
2. Buijs R M, Kalsbeek A: Hypothalamic integration of central and peripheral clocks. Nat. Rev. Neurosci. 2:521-526, 2001
3. Bray M S, Young M E: Circadian rhythms in the development of obesity: potential role for the circadian clock within the adipocyte. Obes. Rev. 8:169-181, 2007
4. Gale J E, Cox H I, Qian J, et al: Disruption of circadian rhythms accelerates development of diabetes through pancreatic beta-cell loss and dysfunction. J. Biol. Rhythms 26:423-433, 2011
5. Shaw E, Tofler G H: Circadian rhythm and cardiovascular disease. Curr. Atheroscler. Rep. 11:289-295, 2009
6. Wyatt J K: Circadian rhythm sleep disorders. Pediatr. Clin. North Am. 58:621-635, 2011
7. Quera Salva M A, Hartley S, Barbot F, et al: Circadian rhythms, melatonin and depression. Curr. Pharm. Des 17:1459-1470, 2011
8. Schibler U, Ripperger J, Brown S A: Peripheral circadian oscillators in mammals: time and food. J. Biol. Rhythms 18:250-260, 2003
9. Jung-Hynes B, Ahmad N: SIRT1 controls circadian clock circuitry and promotes cell survival: a connection with age-related neoplasms. FASEB J. 23:2803-2809, 2009
10. Chang H C, Guarente L: SIRT1 mediates central circadian control in the SCN by a mechanism that decays with aging. Cell 153:1448-1460, 2013
11. Chang H C, Guarente L: SIRT1 mediates central circadian control in the SCN by a mechanism that decays with aging. Cell 153:1448-1460, 2013
12. Hirano A, Yumimoto K, Tsunematsu R, et al: FBXL21 regulates oscillation of the circadian clock through ubiquitination and stabilization of cryptochromes. Cell 152:1106-1118, 2013

13. Sanjust E, Mocci G, Zucca P, et al: Mediterranean shrubs as potential antioxidant sources. Nat. Prod. Res. 22:689-708, 2008
14. Harach T, Aprikian O, Monnard I, et al: Rosemary (*Rosmarinus officinalis* L.) leaf extract limits weight gain and liver steatosis in mice fed a high-fat diet. Planta Med. 76:566-571, 2010
15. Tu Z, Moss-Pierce T, Ford P, et al: Rosemary (*Rosmarinus officinalis* L.) Extract Regulates Glucose and Lipid Metabolism by Activating AMPK and PPAR Pathways in HepG2 Cells. J. Agric. Food Chem. 2013
16. Bakirel T, Bakirel U, Keles O U, et al: In vivo assessment of antidiabetic and antioxidant activities of rosemary (*Rosmarinus officinalis*) in alloxan-diabetic rabbits. J. Ethnopharmacol. 116:64-73, 2008
17. Uezu E: Effects of *Hemerocallis* on sleep in mice. Psychiatry Clin. Neurosci. 52:136-137, 1998
18. Que F, Mao L, Zheng X: In vitro and vivo antioxidant activities of daylily flowers and the involvement of phenolic compounds. Asia Pac. J. Clin. Nutr. 16 Suppl 1:196-203, 2007
19. Wilking M, Ndiaye M, Mukhtar H, et al: Circadian rhythm connections to oxidative stress: implications for human health. Antioxid. Redox. Signal. 19:192-208, 2013
20. Hardeland R, Coto-Montes A, Poeggeler B: Circadian rhythms, oxidative stress, and antioxidative defense mechanisms. Chronobiol. Int. 20:921-962, 2003.
21. U.S. Application Publication No: 2011/0076349
22. WO 2001/080818 A1

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

The foregoing description is illustrative of particular aspects of the invention, but is not meant to be a limitation upon the practice thereof. The following claims, including all equivalents thereof, are intended to define the scope of the invention.

The invention claimed is:

1. A process of altering an expression characteristic of a circadian locomotor output cycles kaput, brain and muscle Arnt-like protein-1, F-box/LRR-repeat protein 3, F-box/LRR-repeat protein 21, or silent mating type information regulation 2 homolog 1 protein in a human or animal in need thereof consisting essentially of:
administering to said human or animal in need thereof a therapeutically effective amount of an extract of rosemary and an extract of *hemerocallis fulva* at an administration time occurring at or between −4 hours to 12 hours after light exposure of the human or animal, wherein said therapeutically effective amount of the extract of rosemary and the extract of *hemerocallis fulva* consists essentially of ursolic acid at 10% or greater by weight.

2. The process of claim 1 said administration time is at or between 0 hours to 12 hours after light exposure.

3. The process of claim 1 said administration time is at or between 1 hours to 3 hours after light exposure or 10-12 hours after light exposure.

4. The process of claim 1 wherein said administration time is at or between −4 hours to 0 hours prior to light exposure.

* * * * *